United States Patent [19]
Kleinschmitt

[11] Patent Number: 5,960,129
[45] Date of Patent: Sep. 28, 1999

[54] METHOD AND APPARATUS FOR DETECTING LIQUID AND GAS SEGMENT FLOW THROUGH A TUBE

[75] Inventor: David Kleinschmitt, Bethel, Conn.

[73] Assignee: Bayer Corporation, Tarrytown, N.Y.

[21] Appl. No.: 08/995,738

[22] Filed: Dec. 22, 1997

[51] Int. Cl.[6] .................................................. G02B 6/00
[52] U.S. Cl. .................. 385/12; 385/13; 385/115; 385/120; 385/147; 250/559.12; 250/227.15
[58] Field of Search ............................. 385/12, 13, 115, 385/120, 147; 250/559.12, 559.43, 227.14, 227.15, 227.17, 227.24

[56] References Cited

U.S. PATENT DOCUMENTS

| | | | |
|---|---|---|---|
| 4,117,727 | 10/1978 | Friswell et al. ........................... | 73/422 |
| 4,130,010 | 12/1978 | Wonn ........................................ | 73/19 |
| 4,235,095 | 11/1980 | Lieberman ................................ | 73/19 |
| 4,312,341 | 1/1982 | Zissimopoulos et al. ............. | 128/214 E |
| 4,344,429 | 8/1982 | Gupton et al. ........................ | 128/214 R |
| 4,366,384 | 12/1982 | Jensen ..................................... | 250/575 |
| 4,367,736 | 1/1983 | Gupton ................................... | 128/214 E |
| 4,599,888 | 7/1986 | Hufton et al. .............................. | 73/19 |
| 4,607,520 | 8/1986 | Dam ........................................... | 73/19 |
| 4,727,277 | 2/1988 | Adams ..................................... | 310/321 |
| 4,784,643 | 11/1988 | Siretchi et al. ......................... | 604/122 |
| 4,884,065 | 11/1989 | Crouse et al. ........................... | 340/632 |
| 4,920,336 | 4/1990 | Meijer ..................................... | 340/619 |
| 5,043,706 | 8/1991 | Oliver ..................................... | 340/603 |
| 5,083,862 | 1/1992 | Rusnak ................................... | 356/237 |
| 5,205,153 | 4/1993 | Hlavinka et al. ....................... | 73/79.03 |
| 5,455,423 | 10/1995 | Mount et al. ............................ | 250/343 |
| 5,466,946 | 11/1995 | Kleinschmitt et al. ............ | 250/559.12 |
| 5,539,386 | 7/1996 | Elliott ..................................... | 340/632 |

*Primary Examiner*—Phan T. H. Palmer
*Attorney, Agent, or Firm*—Orrick Herrington & Sutcliffe LLP

[57] ABSTRACT

A bubble detector/direction sensor for detecting the presence of liquid and gas in a stream of liquid and gas segments flowing through an elongated transparent tube and for sensing the direction of flow of the stream. The sensor has first and second light sources, first and second input fiber optic bundles, and first and second collection fiber optic bundles. The first and second input fiber optic bundles couple the first and second light sources to first and second sides of the tube, respectively, so that light passes through the tube. When the tube is filled with liquid, the light passing therethrough from each light source passes through first and second predetermined regions. When the tube is filled with gas, the light passing therethrough passes outside of the predetermined regions. The first and second collection fiber optic bundles are coupled to the second and first sides of the tube, respectively, outside of the predetermined regions. A circuit is provided for producing signals indicating the presence of liquid in the tube, the presence of gas in the tube, and the direction of flow of liquid and gas through the tube based upon the light received by the first and second collection fiber optic bundles.

18 Claims, 7 Drawing Sheets

METHOD AND APPARATUS FOR DETECTING LIQUID AND GAS SEGMENT FLOW THROUGH A TUBE

FIELD OF THE INVENTION

The present invention is directed to a method and apparatus for discriminating between liquid and gas in a stream of liquid and gas segments flowing through an elongated tube and for sensing the direction of flow of such a segmented stream. The present invention is also directed to a method and apparatus for detecting the presence of a liquid segment in such a segmented stream which contains a marker dye having known absorbance characteristics.

BACKGROUND

In analytical instrumentation systems, such as clinical chemistry analyzers, liquid samples such as blood plasma or urine are often processed by separating each of a number of samples by a gas bubble, typically air, to create a stream of segments and flowing the stream of liquid and gas segments through an elongated tube. As the stream flows through the tube, various analytical measurements are performed. In some systems, the flow of the stream of liquid and gas segments is capable of reversing direction during processing.

In such systems, in order for the processing and analysis to be accurate, it is important to be able to discriminate between the liquid segments and the gas segments and to be able to determine the direction of flow of the stream. Devices which provide this functionality are known in the art and are typically called bubble detectors. One such prior art bubble detector is described in U.S. Pat. No. 5,466,946 to Kleinschmitt et al., hereinafter the '946 patent, the disclosure of which is incorporated herein by reference in its entirety.

FIGS. 1 and 2 are schematic cross-section diagrams of the above described prior art bubble detector described in the '946 patent. As shown in the FIGS. 1 and 2, the bubble detector includes an illumination fiber optic bundle 10 which receives white input light from light source 11 and directs the light through the diameter of a transparent tube 12 through which a liquid and gas segmented stream passes in a direction orthogonal to the longitudinal axis of the tube 12. Located on the side of the tube 12 opposite bundle 10 is a collection fiber optic bundle 14, which directs light to conventional analyzer instrumentation (not shown), and a smaller fiber optic bundle 15. Bundle 15 only receives light extending outside a predetermined zone in which bundle 14 is disposed. The light collected by bundle 15 is input into a photodiode 16 that converts the light to electrical energy. Comparator 17 compares the output of the photodiode 16 to a reference voltage 18 and generates a control signal 19.

As shown in FIG. 1, when the tube 12 contains liquid, the light from the illumination fiber optic bundle 10 is bent or refracted when passing through the liquid filled tube 12 so that substantially none of the light rays extend outside the predetermined zone and reach bundle 15. Under such circumstances, the signal from the photodiode 16 is low, i.e., below the reference voltage 18, so that the comparator 17 produces a control signal 19 having a first level which indicates that there is liquid in the tube 12.

As shown in FIG. 2, when the tube 12 contains a gas such as air, the light rays from the illumination fiber optic bundle 10 are not refracted or bent as severely, and consequently, a significant portion of the light is disposed beyond the predetermined zone and is collected by the bundle 15. As a result, the signal from the photodiode 16 is high, i.e., above the reference voltage 18, so that the comparator 17 produces a control signal 19 having a second level that indicates that a gas is in the tube 12.

The height of bundles 10, 14 and 15 and their proximity to the tube 12 must be chosen to assure sufficient light bending or refraction so that substantially none of the rays impinge upon bundle 15 when liquid is in the tube 12. The particular geometries are described in detail in the '946 patent and thus will not be repeated herein.

FIG. 3 shows another embodiment of the bubble detector described in the '946 patent wherein the direction of flow of a stream of liquid and gas segments is detected in addition to the detection of a liquid/gas interface. As shown in FIGS. 3 and 4, the bubble detector includes two light path channels made up of fiber optic bundles 15 and 15' that share the same illumination fiber bundle 10. The bundles 15 and 15' are spaced apart a distance less than the width of the smallest liquid or gas segment in order to detect the interface between a gas segment and a liquid segment.

The output from each of the bundles 15 and 15' is fed to photodiodes 16 and 16', the outputs of which are received by comparators 17 and 17' and compared to reference voltages 18 and 18' to produce outputs 19 and 19'. The outputs 19 and 19' are applied to logic circuit 20 which produces two output signals 21 and 22, one specifying the fact that a liquid/gas interface has occurred and the other specifying the direction of flow of the stream. The particulars of the logic circuit 20, and the method utilized therein to determine the direction of flow of the stream are described fully in the '946 patent and will not be repeated herein.

Because the bubble detector described in the '946 patent utilizes a single light source 11 and a single illumination fiber optic bundle 10 to direct light through tube 12 for each of the two light path channels, and because the light travels in substantially the same direction in each of the light path channels, there is a tendency for optical cross-talk to occur between the two channels. As a result, some of the light from the first channel may be received by the photodiode dedicated to the second channel and vice versa, thereby creating a signal discrimination problem.

SUMMARY OF THE INVENTION

The present invention relates to a method and apparatus for detecting the presence of a liquid segment and a gas segment in a stream of liquid and gas segments flowing through an elongated transparent tube and for sensing a direction of flow of the stream in the tube.

One aspect of the invention is directed to a bubble detector/direction sensor. One such sensor includes first and second light sources, first and second input fiber optic bundles, and first and second collection fiber optic bundles. The first input fiber optic bundle couples the first light source to the tube on a first side thereof so that light passes through the tube into a first predetermined region on the second side thereof, in response to a liquid segment being present in the tube and outside the first predetermined region on the second side in response to a gas segment being present in the tube. The second input fiber optic bundle couples the second light source to the tube on a second side thereof so that light passes through the tube into a second predetermined region on the first side thereof in response to a liquid segment being present in the tube and outside of the second predetermined region on the first side in response to a gas in the tube.

The first and second collection fiber optic bundles are coupled to the second and first sides of the tube, respectively, and are located outside of the respective predetermined regions. A circuit is coupled to the first and second collection fiber optic bundles. The circuit has a first output indicating a direction of flow of the stream and a second output indicating the presence of at least one of a liquid segment and a gas segment in the tube.

In alternative embodiments, the invention includes an additional collection fiber optic bundle coupled to the second side of the tube. The additional bundle is positioned within the first predetermined region. In these alternative embodiments, the circuit is coupled to the additional bundle and has an output indicating the presence of a liquid segment in the tube containing a marker dye having known absorbance characteristics.

Another aspect of the present invention is directed to a method of detecting the presence of a liquid segment and a gas segment in a stream of liquid and gas segments flowing through an elongated transparent tube and of detecting a direction of flow. One such method includes illuminating the tube at a first position adjacent a first side of the tube with a first light, passing the first light through the tube, and in response to the presence of a liquid segment in the tube, refracting the first light into a first predetermined region, and in response to the presence of a gas segment in the tube, refracting the first light outside of the first predetermined region, and detecting a first amount of light passing through the tube at a second position located adjacent a second side of the tube and outside the first predetermined region. The method also includes illuminating the tube at a third position adjacent the second side of the tube with a second light, passing the second light through the tube, and in response to the presence of a liquid segment in the tube, refracting the second light into a second predetermined region, and in response to the presence of a gas segment in the tube, refracting the second light outside of the second predetermined region, and detecting a second amount of light passing through the tube at a fourth position located adjacent the first side of the tube and outside the second predetermined region. The method then involves determining that at least one of a liquid segment and a gas segment is present in the tube and determining a direction of flow of the stream in the tube based upon the first and second amounts of light.

In alternative embodiments, the method includes detecting a third amount of light passing through the tube at a fifth position located adjacent the second side of the tube and within the first predetermined region and determining that a liquid segment containing a marker dye having known absorbance characteristics is present in the tube based upon the first and third amounts of light and the known absorbance characteristics.

BRIEF DESCRIPTION OF THE DRAWINGS

Further features and advantages of the invention will be apparent upon consideration of the following detailed description of preferred embodiments of the present invention, taken in conjunction with the following drawings, in which like reference characters refer to like parts, and in which.

DETAILED DESCRIPTION OF THE PREFERRED EMBODIMENTS

Figure 1:
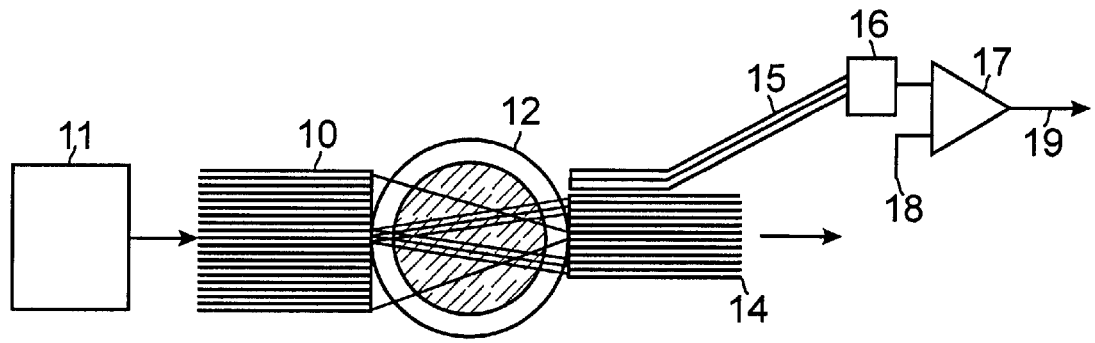
FIG. 1 is a schematic cross-section of a prior art bubble detector showing a tube containing a liquid.
Figure 2:
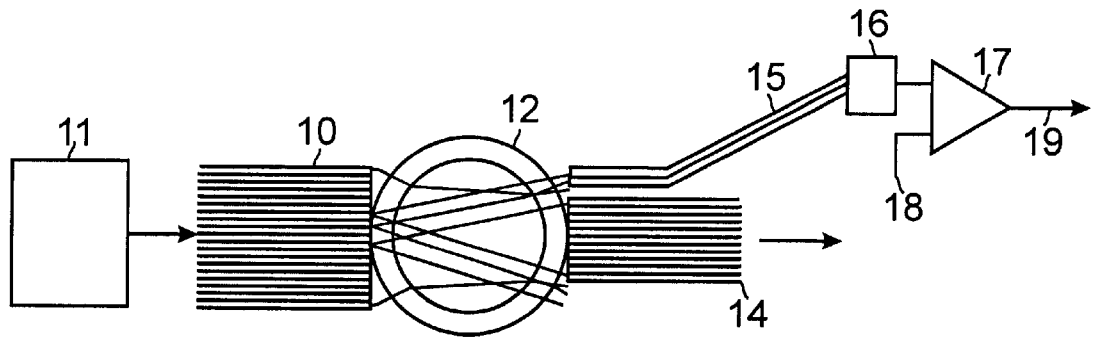
FIG. 2 is a schematic cross-section of a prior art bubble detector showing a tube containing a gas.
Figure 3:
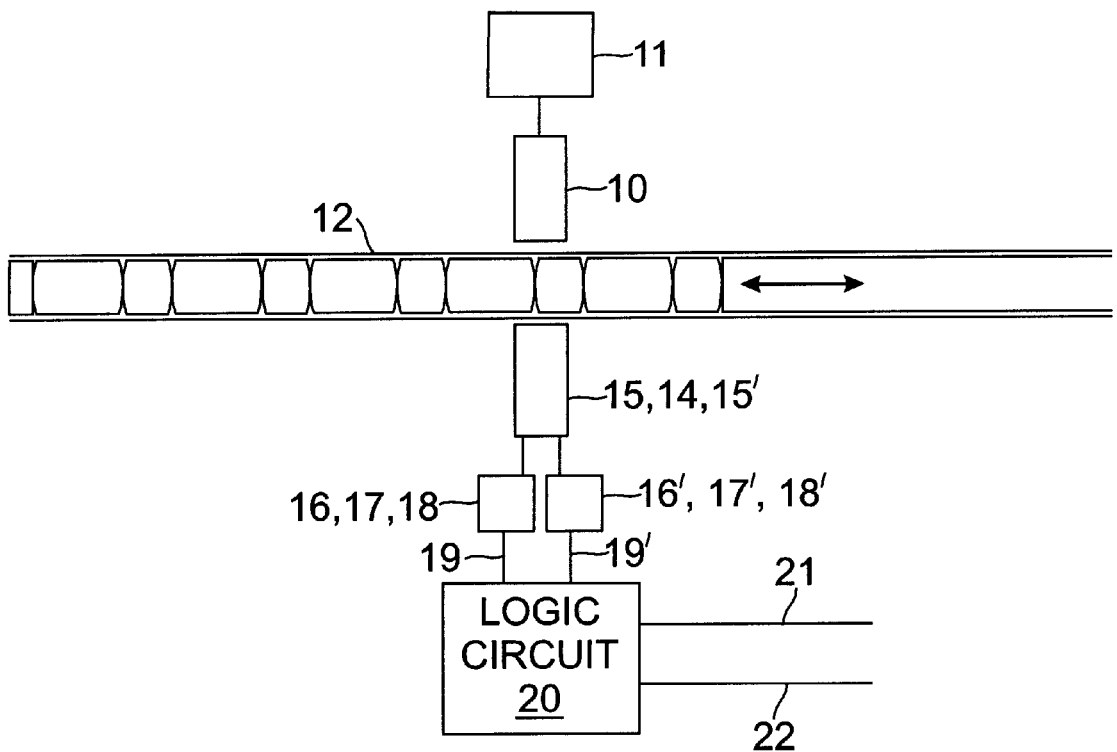
FIG. 3 is a block diagram of a prior art bubble detector that is able to detect the direction of flow of a stream of liquid and gas segments.
Figure 4:
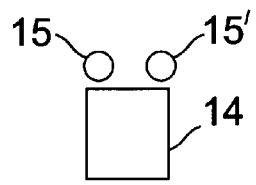
FIG. 4 is a block diagram showing the fiber optic bundles of the prior art bubble detector shown in FIG. 3.
Figure 5:
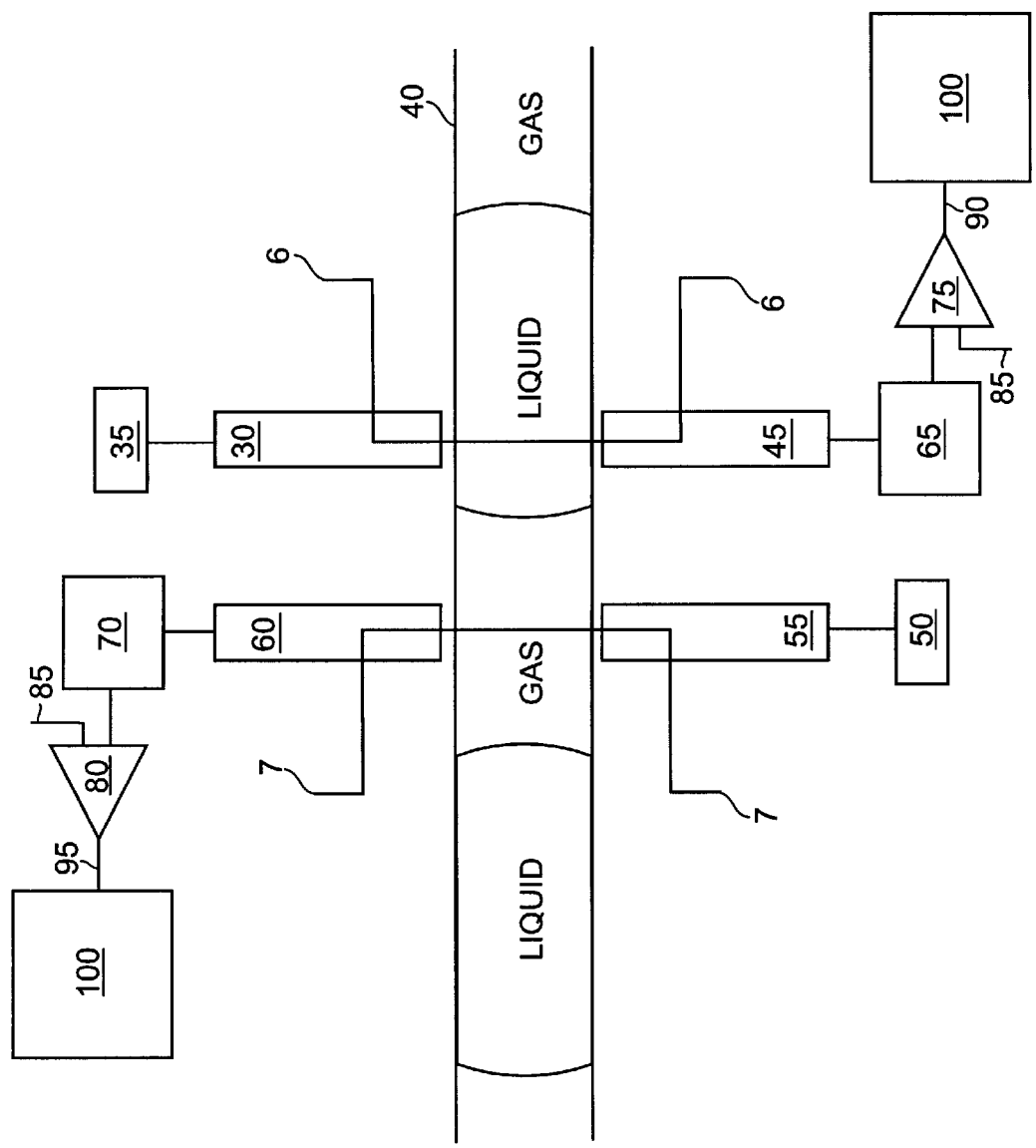
FIG. 5 is a block diagram of the bubble detector/direction sensor according to a first embodiment of the present invention.

Referring to FIG. 5, a block diagram of a bubble detector/direction sensor according to a first embodiment of the present invention is shown. As shown in FIG. 5, illumination fiber optic bundle 30 receives input light from light emitting diode, or LED, 35 and directs the light through the diameter of elongated transparent tube 40 in a direction that is substantially orthogonal to the longitudinal axis of the tube 40. Collection fiber optic bundle 45 is located on the side of the tube 40 opposite the bundle 30. Similarly, illumination fiber optic bundle 55, located on the same side of the tube 40 as collection fiber optic bundle 45, receives input light from LED 50 and directs the light through the diameter of transparent tube 40 in a direction that is substantially orthogonal to the longitudinal axis of the tube 40. Collection fiber optic bundle 60 is located on the side of the tube 40 generally opposite the bundle 55. The term "side of the tube" as used herein means those portions of the tube defined by a plane 42 which intersects the longitudinal axis of the tube and is generally normal thereto, as shown in FIGS. 6 and 7.

Illumination fiber optic bundle 30 and illumination fiber optic bundle 55 must each be positioned with respect to the respective side of the tube 40 so that the direction in which each directs light through the tube 40 will result in substantially no cross-talk therebetween. In a preferred embodiment of present invention, this result is optimally achieved by positioning bundle 30 and bundle 55 with respect to the side of the tube 40 and with respect to one another such that the direction of the light from bundle 30 as it passes through the tube 40 is substantially opposite to the direction of the light from bundle 55 as it passes through the tube. However, it should be understood that it is not essential to position the bundles in this way and that various other positioning schemes which minimize the likelihood of cross-talk are possible, as can be readily determined through empirical study, without departing from the scope and spirit of the present invention.

In addition, bundles 45 and 60 are positioned with respect to tube 40 such that each only receives light which passes outside of a predetermined region as defined below. In particular, as shown in FIG. 6, when the tube 40 contains liquid, the light from either the bundle 30 or 55 is bent or refracted when passing through the tube 40 so that substantially none of the light rays pass through an area defined by the outer edges of bundle 45 or 65. Instead, substantially all of the light rays pass through an area outside of the outer edges of bundle 45 or 65. Thus, the predetermined region described above is defined as that area in which substantially all of the light rays pass when the tube contains a liquid. Furthermore, as shown in FIG. 7, when the tube 40 contains a gas such as air, the light from either bundle 30 or 55 is not bent or refracted as severely, meaning it is not bent or refracted such that it passes through the predetermined region described above, and, consequently, substantially all of the light from bundle 30 or 55 passes through the tube in the area outside of the predetermined region and a significant portion is collected by either bundle 45 or 60.

Figure 6:
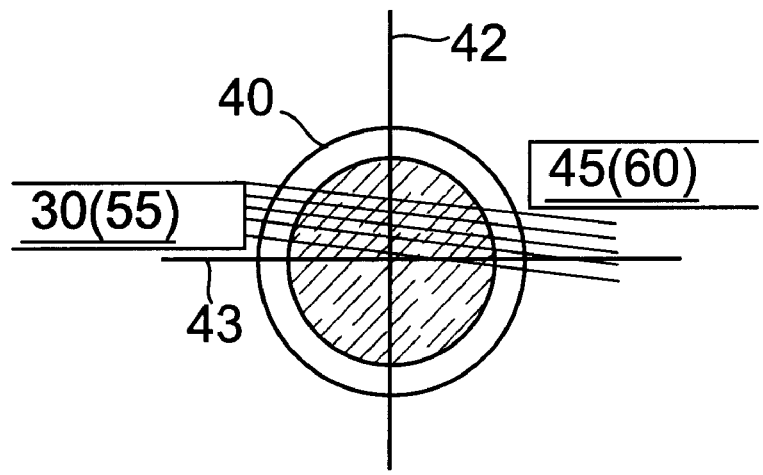
FIG. 6 is a schematic cross-section taken along line 6—6 of FIG. 5 showing a tube containing a liquid.
Figure 7:
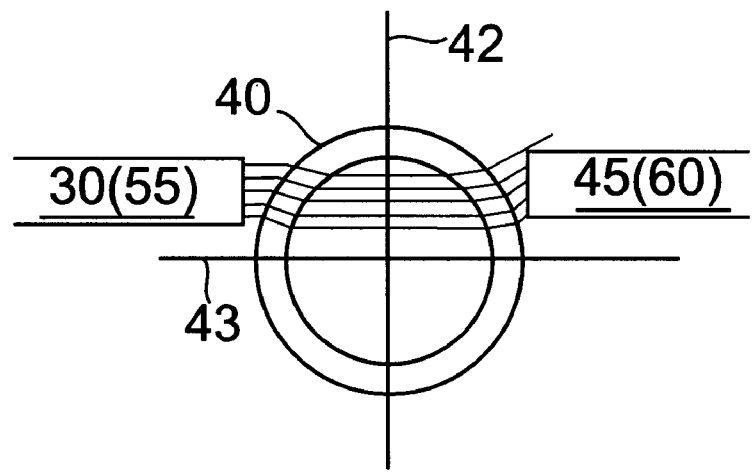
FIG. 7 is a schematic cross-section taken along line 7—7 of FIG. 5 showing a tube containing a gas.

Thus, referring to FIGS. 6 and 7, the dimensional placement of bundles 30 and 55 and bundles 45 and 60 with respect to plane 43 which intersects the longitudinal axis of the tube 40 is critical. The placement must be such that the light rays when passing through a liquid filled tube 40 are refracted into the predetermined region described above not occupied by either the bundle 45 or the bundle 60, whichever the case may be, and must also be such that the light rays when passing through a gas filled tube 40 are not so refracted and instead pass outside of the predetermined region and into an area occupied by either the bundle 45 or the bundle 60, whichever the case may be. The exact dimensions with respect to plane 43 are a function of the diameter of the tube 40, the refractive index of the liquid in the tube 40, and the refractive index of the tube itself. The optimal dimensions for the placement of bundles 30 and 55 and bundles 45 and 60 for a particular application of the present invention will be readily apparent to one of ordinary skill in the art based upon the above described factors.

Furthermore, as described in U.S. Pat. No. 5,399,497 to Kumar et al, it may be advantageous to use a film of isolating liquid, such as oil, on the inner surface of the tube 40 in order to prevent residual liquid from sticking to the inner surface of the tube 40 as the stream of liquid and gas segments passes through the tube 40. When such an isolating liquid is used in connection with the present invention, it is preferable that bundles 30 and 55 and bundles 45 and 60 be placed in the upper half of tube 40, meaning above the plane 43 as shown in FIGS. 6 and 7, so that the light path is through the upper half of the tube 40. This placement is preferred because the isolating liquid tends to pool in the lower half of the tube 40 at low stream velocities, which would result in decreased performance if bundles 30 and 55 and bundles 45 and 60 were placed in the lower half of tube 40 because the light path would be through the lower half of the tube 40 and thus through the pooled isolating liquid. Of course, if no isolating liquid is used, then placement of the bundles 30 and 55 and bundles 45 and 60 in the upper half of the tube 40 as compared to the lower half of the tube 40 is not so important.

Referring again to FIG. 5, the light collected by bundles 45 and 60 is input into photodetector/amplifier integrated circuit devices 65 and 70, respectively, in order to convert the light into electrical energy. Suitable photodetector/amplifier integrated circuit devices are, for example, part no: OPT101 manufactured by Burr-Brown. It should be readily apparent to one of ordinary skill in the art that instead of using an integrated circuit device to perform the function of photodetector/amplifier integrated circuit devices 65 and 70, discrete photodetector and amplifier elements can be used. The outputs of the photodetector/amplifier integrated circuit devices 65 and 70 are respectively received by comparators 75 and 80 which compare the output of each photodetector/amplifier 65 and 70 to a reference voltage 85 to generate control signals 90 and 95.

Thus, when the tube 40 contains liquid at a point between either bundles 30 and 45 or bundles 55 and 60, the signal output by photodetector/amplifier integrated circuit devices 65 and 70, respectively, is low, i.e., below the reference voltage 85, so that comparators 75 and 80, respectively, produce control signals 90 and 95, respectively, having a first level which indicates that there is liquid in the tube 40. When the tube 40 contains a gas such as air at a point between either bundles 30 and 45 or bundles 55 and 60, the signal output by photodetector/amplifier integrated circuit devices 65 and 70, respectively, is high, i.e., greater than the reference voltage 85, so that comparators 75 and 80 produce control signals 90 and 95, respectively, having a second level which indicates that there is gas in the tube 40.

Preferably, bundle 30 and bundle 55 are separated along the longitudinal axis of tube 40 by a distance that is smaller than the width of the smallest liquid or gas segment flowing through the tube 40. This orientation allows for the detection of the interface between any gas segment and any liquid segment.

The control signals 90 and 95 are each fed to logic circuit 100. Logic circuit 100 is preferably implemented using conventional logic embodied in software using an integrated circuit chip or a solid state machine such that it outputs signals indicating the presence of either a liquid or gas segment and the direction of flow of the stream of liquid and gas segments. The particular set of logic states used to implement logic circuit 100 is described fully in the '946 patent and will not be repeated herein. It should be noted, however, that logic circuit 100 could be implemented in numerous ways by one of ordinary skill in the art to achieve the desired functionality without departing from the spirit and scope of the invention.

Figure 8:
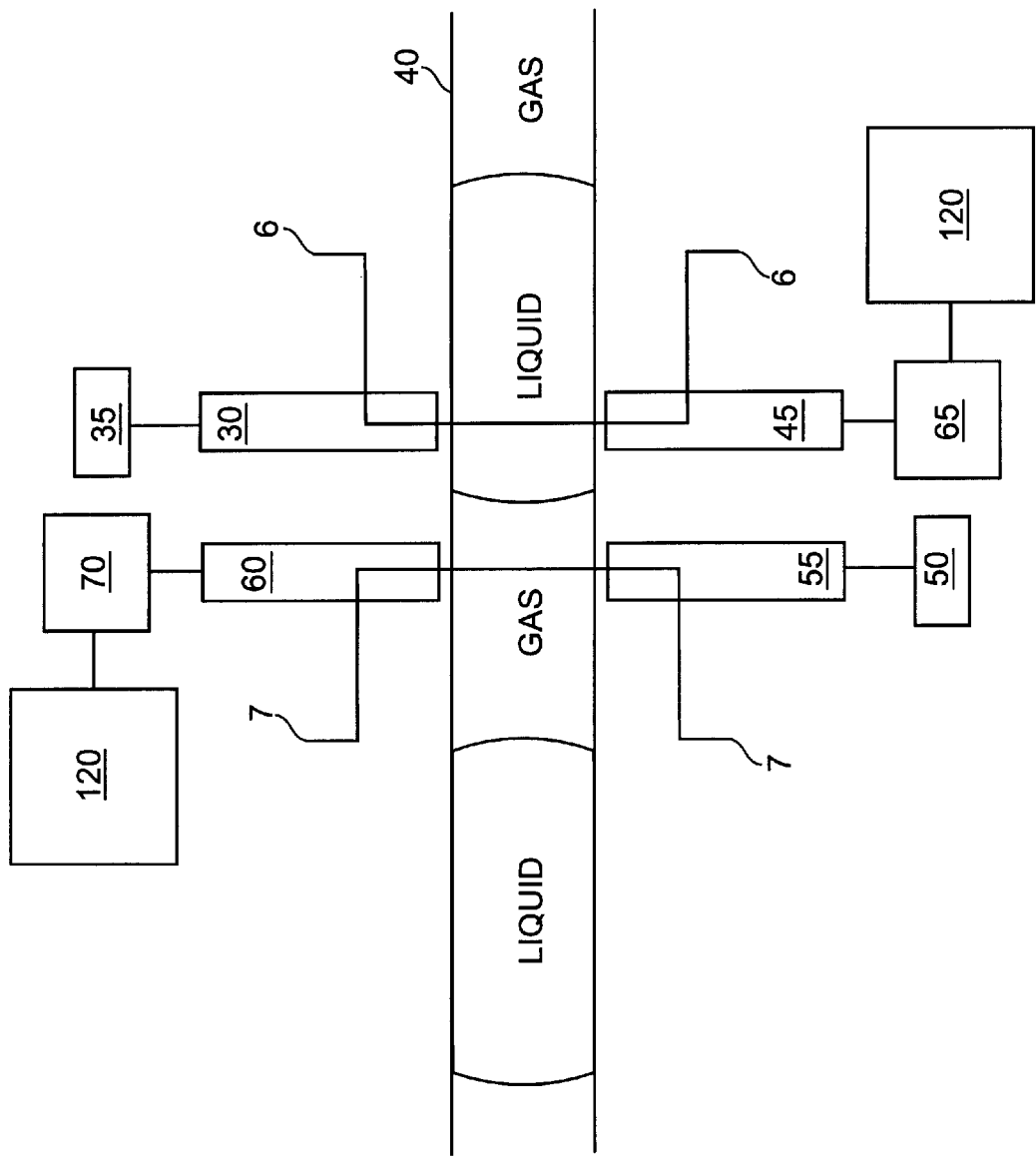
FIG. 8 is a block diagram of the bubble detector/direction sensor according to a second, preferred embodiment of the present invention.

Referring to FIG. 8, a block diagram of a bubble detector/direction sensor according to a second, preferred embodiment of the present invention is shown. In the second, preferred embodiment of FIG. 8, comparators 75 and 80, reference voltage 85, controls signals 90 and 95, and logic circuit 100 shown in FIG. 5 are replaced by computer 120. In other words, the outputs of photodetector/amplifier integrated circuit devices 65 and 70 are fed directly into computer 120. In this performed embodiment, the functionality and logic provided by comparators 75 and 80, reference voltage 85, control signals 90 and 95, and logic circuit 100 is provided completely by software loaded into computer 120. The computer 120 is then able to output signals indicating the direction of flow of the stream and the presence of either liquid or gas in the tube 40. The details of how to implement this functionality in software would be readily apparent to one of ordinary skill in the art and thus will not be provided herein. The embodiment shown in FIG. 8 is preferred because it eliminates the need for additional hardware components.

As noted above, the fact that in the preferred embodiment of the present invention bundles 30 and 55 are disposed on opposite sides of the tube 40 so that light travels through the tube 40 from bundle 30 in a direction substantially opposite to light travelling through the tube 40 from bundle 55 ensures that the bubble detector/direction sensor of the present invention is effectively immune from optical crosstalk between the two light path channels. This, advantageously, overcomes the aforementioned deficiency of the prior art.

In addition, it is common in analytical instrumentation that utilizes a flowing stream of liquid and gas segments to periodically insert in the stream at known locations liquid segments containing a marker dye having known absorbance characteristics. This is done to keep track of the flowing segmented stream as it moves throughout the system. Specifically, the liquid segments containing the marker dye can be detected and used as indicators of the location of particular segments in the stream.

Figure 9A:
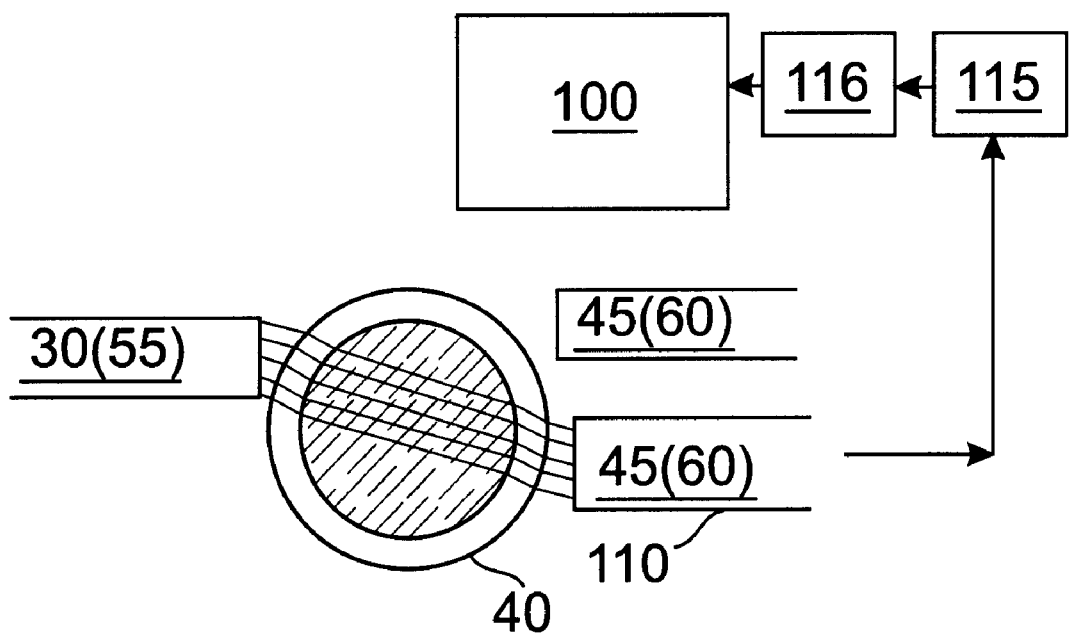
FIGS. 9A and 9B are schematic cross-sections of the bubble detector/direction sensor according to alternative embodiments of the present invention which are capable of detecting the presence of a marker dye.

Referring to FIG. 9A, an alternative embodiment of the present invention is shown in which a liquid segment containing a marker dye also is able to be detected. Specifically, collection fiber optic bundle 110 is positioned adjacent the tube 40 on a side of the tube 40 opposite either bundle 30 or bundle 55. Furthermore, bundle 110 is positioned within the predetermined region discussed with reference to FIGS. 6 and 7 such that when the tube 40 contains liquid, the light from either bundle 30 or bundle 55 is bent or refracted when passing through the tube and is directed to bundle 110. The light collected by bundle 110 is output to photodetector 115 and then to amplifier 116 to convert the light to electrical energy. The discrete photodetector and amplifier components 115 and 116 can be replaced by a photodetector/amplifier integrated circuit device as described above.

The output of amplifier 116 is input into logic circuit 100. Logic circuit 100 is implemented using conventional logic such that, when the bubble detector/direction sensor determines that liquid is present in the tube 40 as described above, logic circuit 100 can determine whether the liquid is a sample segment or a segment containing marker dye using the light collected by bundle 110 and the known absorbance characteristics of the particular marker dye or dyes used. Specifically, when a liquid segment without marker dye is present in the tube, a particular amount of light will reach the bundle 110 due to the characteristics of the liquid samples. This amount of light will be substantially consistent among all of the liquid segments that are liquid samples to be analyzed. However, when a liquid segment containing a marker dye is present in the tube, a different, known amount of light will reach the bundle 110 depending upon the particular absorbance characteristics of the marker dye used. Thus, the logic circuit 100 is able to distinguish between liquid samples with and without marker dye based upon the amount of light received by the bundle 110. As a result, the location of particular segments in the stream can be determined and tracked. The particulars necessary to implement conventional logic in logic circuit 100 to achieve the desired functionality would be readily apparent to one of ordinary skill in the art and thus will not be discussed herein.

Figure 9B:
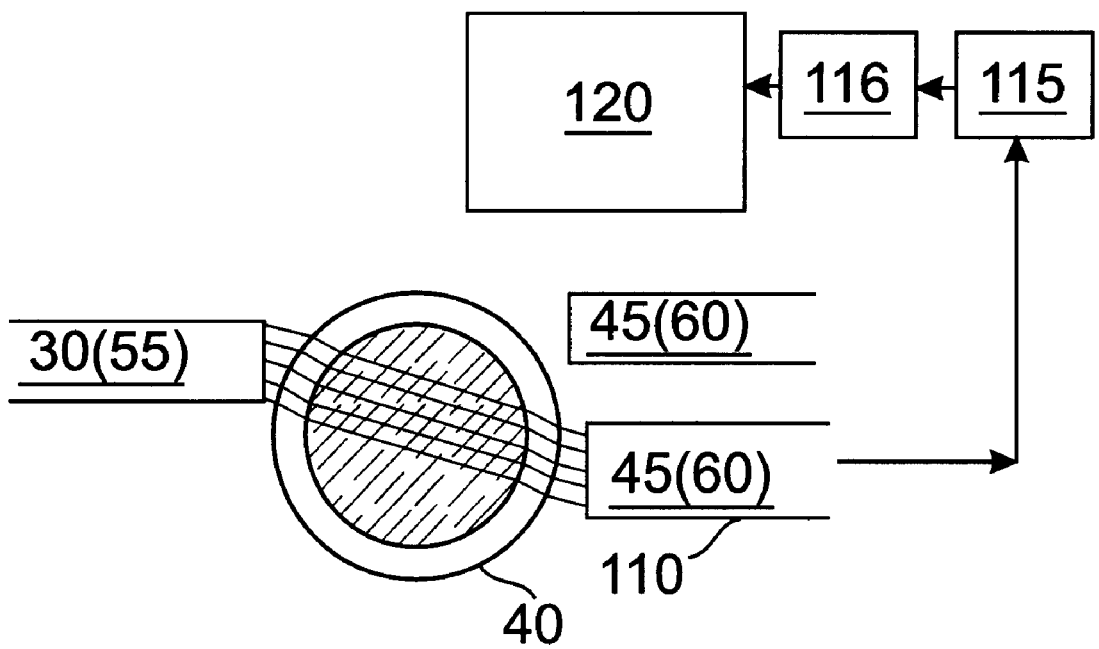

Referring to FIG. 9B, a further alternative embodiment of the present invention is shown in which a liquid segment containing a marker dye is also able to be detected and in which the logic circuit 100 shown in FIG. 9A is replaced with computer 120. Computer 120 is loaded with software which performs all of the functionality of logic circuit 100 described above. The details of how to implement this functionality in software would be readily apparent to one of ordinary skill in the art and thus will not be discussed herein.

One skilled in the art will appreciate that the present invention can be practiced by other than the described embodiments, which are presented for purposes of illustration, and not of limitation.

We claim:

1. An apparatus for detecting the presence of a liquid segment and a gas segment in a flowing stream of liquid and gas segments and a direction of flow, comprising:

an elongated transparent tube having a longitudinal axis, a first side and a second side, the liquid and gas segments being flowable through said tube in at least one of a first direction and a second direction along said longitudinal axis;

a first light source;

a first input fiber optic bundle coupling said first light source to said first side of said tube so that light from said first light source passes through said tube into a first predetermined region in response to a liquid segment being present in the tube and outside of the first predetermined region in response to a gas segment being present in the tube;

a first collection fiber optic bundle coupled to said second side of said tube and positioned outside said first predetermined region;

a second light source;

a second input fiber optic bundle coupling said second light source to said second side of said tube so that light from said second light source passes through said tube into a second predetermined region in a response to a liquid segment being present in the tube and outside of the second predetermined region in response to a gas segment being present in the tube;

a second collection fiber optic bundle coupled to said first side of said tube and positioned outside said second predetermined region; and a circuit coupled to said first and second collection fiber optic bundles having a first output indicating a direction of flow of the stream through such tube and a second output indicating the presence of at least one of a liquid segment and a gas segment in the tube.

2. An apparatus according to claim 1, wherein said first input fiber optic bundle is positioned with respect to said tube such that said first light passes through said tube in a first direction orthogonal to said longitudinal axis of said tube and said second input fiber optic bundle is positioned with respect to said tube such that said second light passes through said tube in a second direction orthogonal to said longitudinal axis of said tube, said first direction and said second direction being substantially opposite one another.

3. An apparatus according to claim 1, wherein said first and second light sources comprise light emitting diodes.

4. An apparatus according to claim 1, wherein said circuit comprises:

a first photodetector coupled to an output of said first collection fiber optic bundle, an output of said first photodetector being input into a first amplifier;

a second photodetector coupled to an output of said second collection fiber optic bundle, said second photodetector being coupled to a second amplifier;

a first comparator coupled to an output of said first amplifier and a second comparator coupled to an output of said second amplifier, said first and second comparators each having a reference voltage input thereto; and a logic circuit having input thereto an output of said first comparator and an output of said second comparator.

5. An apparatus according to claim 1, wherein said circuit comprises:

a first photodetector coupled to an output of said first collection fiber optic bundle, an output of said first photodetector being input into a first amplifier;

a second photodetector coupled to an output of said second collection fiber optic bundle, said second photodetector being coupled to a second amplifier; and a computer having software coupled to an output of said first amplifier and to an output of said second amplifier.

6. An apparatus according to claim 1, wherein said first input fiber optic bundle and said second input fiber optic bundle are separated along said longitudinal axis of said tube by a distance less than a width of a smallest liquid or gas segment in said stream.

7. An apparatus according to claim 1, further comprising a third collection fiber optic bundle coupled to said second side of said tube and positioned within said first predetermined region, wherein said circuit is coupled to said third collection fiber optic bundle and has a third output indicating the presence of a liquid segment in the tube containing a marker dye having known absorbance characteristics.

8. An apparatus for detecting the presence of a liquid segment containing a marker dye having known absorbance characteristics in a flowing stream of liquid and gas segments, comprising:

an elongated transparent tube having a longitudinal axis, a first side and a second side;

a light source;

an input fiber optic bundle coupling said light source to said first side of said tube so that light from said light source passes through said tube into a predetermined region in response to a liquid segment being present in the tube and outside of the predetermined region in response to a gas segment being present in said tube;

a first collection fiber optic bundle coupled to said second side of said tube and positioned outside said predetermined region;

a second collection fiber optic bundle coupled to said second side of said tube and positioned within said predetermined region; and a circuit coupled to said first and second collection fiber optic bundles having an output indicating the presence of a liquid segment containing said marker dye in said tube.

9. An apparatus according to claim 8, wherein said circuit has a second output indicating the presence of at least one of a gas segment and a liquid segment in said tube.

10. An apparatus according to claim 8, wherein said light source comprises a light emitting diode.

11. An apparatus according to claim 8, wherein said circuit comprises:

a first photodetector coupled to an output of said first collection fiber optic bundle, an output of said first photodetector being input into a first amplifier;

a second photodetector coupled to an output of said second collection fiber optic bundle, an output of said second photodetector being input into a second amplifier;

a comparator coupled to an output of said first amplifier, said comparator having a reference voltage input thereto; and a logic circuit having input thereto an output of said comparator and an output of said second amplifier.

12. An apparatus according to claim 8, wherein said circuit comprises:

a first photodetector coupled to an output of said first collection fiber optic bundle, an output of said first photodetector being input into a first amplifier;

a second photodetector coupled to an output of said second collection fiber optic bundle, an output of said second photodetector being input into a second amplifier; and a computer having software coupled to an output of said first amplifier and to an output of said second amplifier.

13. A method of detecting the presence of a liquid segment and a gas segment in a stream of liquid and gas segments flowing through an elongated transparent tube and of detecting a direction of flow, said elongated transparent tube having a longitudinal axis, a first side and a second side, said method comprising:

illuminating said tube at a first position adjacent said first side of said tube with a first light;

passing said first light through said tube, and in response to the presence of a liquid segment in said tube, refracting said first light into a first predetermined region, and in response to the presence of a gas segment in said tube, refracting said first light outside of the first predetermined region;

detecting a first amount of light passing through said tube at a second position located adjacent a second side of said tube and outside said first predetermined region;

illuminating said tube at a third position adjacent said second side of said tube with a second light;

passing said second light through said tube, and in response to the presence of a liquid segment in said tube, refracting said second light into a second predetermined region, and in response to the presence of a gas segment in said tube, refracting said second light outside of the second predetermined region;

detecting a second amount of light passing through said tube at a fourth position located adjacent said first side of said tube and outside said second predetermined region; and determining that at least one of a liquid segment and a gas segment is present in said tube and determining a direction of flow of said stream in said tube based upon said first amount of light and said second amount of light.

14. A method according to claim 13, wherein said first light is passed through said tube in a first direction orthogonal to said longitudinal axis of said tube and said second light is passed through said tube in a second direction orthogonal to said longitudinal axis of said tube, said first direction and said second direction being substantially opposite one another.

15. A method according to claim 13, wherein said first position and said third position are separated along said longitudinal axis of said tube by a distance less than a width of a smallest liquid or gas segment in said stream.

16. A method according to claim 13, further comprising:

detecting a third amount of light passing through said tube at a fifth position located adjacent said second side of said tube and within said first predetermined region; and determining that a liquid segment containing a marker dye having known absorbance characteristics is present in said tube based upon said first and third amounts of light and said known absorbance characteristics.

17. A method of detecting the presence of a liquid segment containing a marker dye having known absorbance characteristics in a stream of liquid and gas segments flowing through an elongated transparent tube, said elongated transparent tube having a longitudinal axis, a first side and a second side, said method comprising:

illuminating said tube at a first position adjacent said first side of said tube with a light;

passing said light through said tube, and in response to the presence of a liquid segment in said tube, refracting said light into a predetermined region, and in response to the presence of a gas segment in said tube, refracting said light outside of the first predetermined region;

detecting a first amount of light passing through said tube at a second position located adjacent said second side of said tube and outside said predetermined region;

detecting a second amount of light passing through said tube at a third position located adjacent said second side of said tube;

determining that a liquid segment containing a marker dye having known absorbance characteristics is present in said tube based upon said first and second amounts of light and said known absorbance characteristics.

18. A method according to claim 17, further comprising determining that at least one of a liquid segment and a gas segment is present in said tube, based upon said first amount of light.

* * * * *